United States Patent [19]

Hosohara et al.

[11] Patent Number: 5,623,203
[45] Date of Patent: Apr. 22, 1997

[54] REMOTE FIELD FLAW SENSOR INCLUDING AN ENERGIZING COIL, FIRST AND SECOND RECEIVING COIL GROUPS ORIENTED PERPENDICULAR AND A THIRD RECEIVING COIL ORIENTED PARALLEL TO PIPE

[75] Inventors: Yasuharu Hosohara, Yokohama; Yoshikazu Chiba, Toride; Akira Kinoshita, Matsubara; Masanori Akita, Aichi-ken; Takashi Sumi, Tokai; Toshihide Kawabe, Kure, all of Japan

[73] Assignees: Tokyo Gas Co., Ltd.; Osaka Gas Co., Ltd.; Toho Gas Co., Ltd.; CXR Corporation, all of, Japan

[21] Appl. No.: 506,759

[22] Filed: Jul. 26, 1995

[30] Foreign Application Priority Data

Aug. 1, 1994 [JP] Japan .................................... 6-180108

[51] Int. Cl.⁶ .......................... G01N 27/72; G01N 33/12
[52] U.S. Cl. .............................................. 324/220; 324/242
[58] Field of Search .................................. 324/219, 220, 324/221, 225, 239, 243, 326, 329, 232

[56] References Cited

U.S. PATENT DOCUMENTS

| | | | |
|---|---|---|---|
| 3,443,211 | 5/1969 | Wood et al. | 324/220 |
| 4,292,588 | 9/1981 | Smith | 324/221 |
| 4,808,924 | 2/1989 | Cecco et al. | 324/220 |
| 4,808,927 | 2/1989 | Cecco et al. | 324/220 |
| 5,049,817 | 9/1991 | Cecco et al. | 324/220 |
| 5,117,182 | 5/1992 | Cecco et al. | 324/220 |
| 5,119,023 | 6/1992 | Lloyd | 324/239 |
| 5,461,312 | 10/1995 | Hosohara et al. | 324/220 |

*Primary Examiner*—Sandra L. O'Shea
*Assistant Examiner*—Roger C. Phillips
*Attorney, Agent, or Firm*—Lorusso & Loud

[57] ABSTRACT

A flaw sensor for a metal pipe has an exciting coil for generating remote field eddy currents in the pipe. First and second groups of receiving coils are spaced from the exciting coil by respective distances along the axis of the pipe in a region of the generated remote field eddy currents. The first and second groups have respective pluralities of receiving coils with axes perpendicular to the pipe axis and disposed circumferentially about the pipe axis at predetermined angular increments wherein the receiving coils of the second group are staggered relative to the receiving coils of the first group. A third receiving coil is disposed coaxially with the pipe at still another distance from the exciting coil along the pipe axis but also in the region of the generated remote field eddy currents. When a defect in the thickness of the metal pipe is encountered, a magnetic field caused by the defect to be perpendicular to the axis of the pipe is detected by one or more of the receiving coils of the first and/or second group. The third receiving coil detects phase changes to the magnetic field generated parallel to the pipe by the eddy currents. A ratio of phase changes produced by a standard thickness of a reference pipe and a sample subject pipe is used as a correction factor for detected phase changes in a defective pipe to accurately calculate the defective wall thickness.

4 Claims, 7 Drawing Sheets

REMOTE FIELD FLAW SENSOR INCLUDING AN ENERGIZING COIL, FIRST AND SECOND RECEIVING COIL GROUPS ORIENTED PERPENDICULAR AND A THIRD RECEIVING COIL ORIENTED PARALLEL TO PIPE

BACKGROUND OF THE INVENTION

1. Field of the Invention

The present invention relates to a flaw detector or discriminator and a flaw detection method for metal pipes and, more particularly, to a flaw detector or discriminator and a flaw detection method for maintaining pipelines such as underground gas pipelines, chemical plant pipelines and heat exchanger pipelines by means of remote field eddy current examination.

2. Description of the Related Art

Hitherto, a remote field eddy current sensor using a remote field eddy current examination method in detecting corrosion or the like existing in interior and exterior walls of a metal pipe such as an underground gas pipeline, a chemical pipeline or a heat exchanger pipeline is known in the art. As shown in FIG. 8, a remote field eddy current sensor 1 has an exciting coil 2 and one or more receiving coils 8 disposed in the longitudinal direction of the pipe and separated from the exciting coil 2 by a distance about twice the diameter of the pipe. The remote field eddy current sensor 1 is connected to a signal transmission cable 4 and, when it is inserted in a pipe 5, is allowed to run within the pipe 5 by means of a driving mechanism controlled from outside. The remote field eddy current sensor 1, together with an exciting signal generating means for applying an exciting signal to the exciting coil 2 of the remote field eddy current sensor 1 from outside the pipe via the signal transmission cable 4 and a flaw data generating means for creating flaw data by receiving measured signals from the receiving coils 3 of the remote field eddy current sensor 1 via the signal transmission cable 4, constitutes a flaw detector for metal pipes.

An exciting voltage from several volts to several tens of volts is applied to the exciting coil 2 of this remote field eddy current sensor 1 and an electromagnetic wave having a relatively low frequency normally from several tens of hertz to several hundreds of hertz is used as the exciting signal applied to the exciting coil 2. Electromagnetic waves caused by the remote field eddy current generated from the exciting coil 2 to which the exciting signal has been input propagate by indirect propagation passing through the thickness of the metal pipe or direct propagation in the pipeline as a wave guide. In the case of the latter however, the electromagnetic wave rapidly attenuates and is not substantially propagated because the frequency of the electromagnetic wave caused by the remote field eddy current is much lower than that of the pipeline. Conversely, in the case of the former, the electromagnetic wave caused by the remote field eddy current propagates through the thickness of the metal pipe while slowly attenuating and at the same time, part of it permeates into and again passes through the thickness of the metal pipe and is received by the receiving coil 3. Although the received signal detected by the receiving coil 3 is very weak (several µV to several tens of µV), the phase thereof is changed due to a skin effect in passing through the thickness of the metal pipe. Because this phase change has good linearity relative to the thickness of the metal pipe, a decrease of the thickness of the metal pipe may be accurately detected and the existence of corrosion and the depth of flaws on the interior and exterior walls of the metal pipe may be reliably detected by detecting the phase difference between the exciting signal and the measured signal.

However, the remote field eddy current sensor 1 described above has a drawback in that although the electromagnetic wave caused by the remote field eddy current and transmitted through the thickness of the undamaged metal pipe having no corrosion is transmitted mainly in parallel with the axis of the metal pipe and is favorably received by the receiving coil installed coaxially with the metal pipe, it cannot detect phase change accurately because an electromagnetic wave vertical to the interior wall of the pipe is generated at a defective portion and the receiving coil installed concentrically with the metal pipe cannot adequately receive this electromagnetic wave vertical to the longitudinal direction of the metal pipe.

Further, because the electromagnetic wave caused by the remote field eddy current transmitted through the thickness of the metal pipe is influenced by conditions such as the permeability and electrical conductivity of the material of the metal pipe and the frequency of the exciting signal, the phase difference of the measured signal output from the receiving coil disperses among pipes of different materials, even if an equal exciting voltage is applied to the exciting coil. Due thereto, the remote field eddy current sensor 1 has the problem that it cannot accurately evaluate the depth of a flaw in pipes having different materials from a predetermined relationship between the phase difference and the thickness.

The remote field eddy current sensor 1 also has the problem that it is difficult to detect a flaw by a single scan and scanning must be repeated many times when testing a pipe having a relatively large aperture (e.g. 200 A=e.g. outer diameter 225.8 mm, thickness 10.2 mm) with a remote field eddy current sensor in which one receiving coil is installed.

Accordingly, it is a primary object of the present invention to solve the aforementioned problems by providing a flaw sensor for metal pipes which can detect a magnetic field generated from a defective portion and can effectively test the entire interior circumferential surface of the metal pipe by a single scan using a plurality of receiving coils whose axes are disposed at right angles to the longitudinal direction of the metal pipe and which are provided in the circumferential direction of the pipe.

It is another object of the present invention to provide a method for detecting flaws in metal pipes which allows accurate evaluation of the existence of corrosion and the depth of the flaw in the metal pipe corresponding to the material of the metal pipe by detecting a phase difference which changes depending on the magnetic characteristics entailed by a difference in the material used to produce the metal pipe.

SUMMARY OF THE INVENTION

In order to achieve the aforementioned objects, a flaw sensor for metal pipes of the present invention comprises an exciting coil for generating a remote field eddy current in a metal pipe when an exciting signal is applied; a first receiving coil group comprising a plurality of first receiving coils which are separated from the exciting coil by a predetermined distance in the longitudinal direction of the pipe, axes of which are perpendicular to the longitudinal direction of the metal pipe, and which are disposed at predetermined intervals in the circumferential direction of the metal pipe to receive a reception signal caused by the remote field eddy current; a second receiving coil group comprising a plurality of second receiving coils which is separated from the first receiving coil group by a predetermined distance, axes of which are perpendicular to the longitudinal direction of the metal pipe, and which are disposed at positions staggered from the first receiving coils to receive the reception signal caused by the remote field eddy current; and a third receiving coil disposed so that an axis thereof is coaxial with the longitudinal direction of the metal pipe.

Further, a flaw detecting method for metal pipes of the present invention comprises steps of generating a remote field eddy current in an undamaged metal pipe by applying an exciting signal to an exciting coil; receiving a reception signal caused by the remote field eddy current by means of a receiving coil; detecting a phase difference between a detection signal from the receiving coil and the exciting signal; detecting a correction factor of the metal pipe by comparing it with a reference phase difference of a reference metal pipe previously measured; and converting the phase difference of the measured signal from the receiving coil into a phase difference corresponding to the reference metal pipe by the correction factor to detect a thickness of the defective portion of the metal pipe from the relationship between the reference phase difference and the thickness.

The flaw detecting method for metal pipes of the present invention, according to another aspect thereof, comprises the steps of generating the remote field eddy current in the metal pipe by applying the exciting signal to the exciting coil; receiving the reception signal caused by the remote field eddy current by means of the third receiving coil whose axis is coaxial with the longitudinal direction of the metal pipe; detecting a phase difference from the third receiving coil as a specific phase difference of the metal pipe, receiving the reception signal caused by the remote field eddy current by means of the first receiving coils which are separated from the exciting coil by a predetermined distance in the longitudinal direction of the pipe, whose axes are perpendicular to the longitudinal direction of the metal pipe and which are disposed at predetermined intervals in the circumferential direction of the metal pipe and/or second receiving coils which are separated from the first receiving coils by a predetermined distance, whose axes are perpendicular to the longitudinal direction of the metal pipe and which are disposed at positions staggered from the first receiving coils, after detecting a correction factor of the metal pipe by comparing the phase difference of the measured signal with a reference phase difference of a reference metal pipe previously measured; detecting the phase difference of the measured signal from the first receiving coil/second receiving coil; and converting it into a phase difference corresponding to the reference metal pipe by the correction factor to detect the thickness of the defective portion of the metal pipe from the relationship of the thickness of the reference metal pipe and the reference phase difference.

When the exciting signal is applied to the exciting coil, the remote field eddy current is generated in the metal pipe. When the metal pipe is a sound metal pipe having no defective portions, the magnetic field caused by the remote field eddy current is reliably detected by the third receiving coil which is disposed so that its axis runs parallel with the longitudinal direction of the metal pipe, because the magnetic field takes a magnetic path parallel with the axis of the metal pipe and the specific phase difference of the sound metal pipe is detected. When there is a defective portion in the thickness of the metal pipe, a magnetic field is also formed in the direction perpendicular to the axis of the metal pipe, so that it is reliably detected by the first and second receiving coils disposed so that their axes run parallel with the magnetic field even if the magnetic field generated at the defective portion is very weak.

Because the second receiving coils are staggered from the first receiving coils and the receiving coils are provided covering the inner circumference of the pipe, a flaw which has not been detected by the first receiving coil group because it has passed between the first receiving coils is inevitably detected by the second receiving coil group, allowing detection of whether a flaw exists along the entire circumference of the pipe by a single scan.

Further, prior to testing the metal pipe, a reference phase difference is measured on various thicknesses of a reference metal pipe to be referred to in order to obtain the relationship between the thickness and the reference phase difference of the reference metal pipe, a remote field eddy current is generated in the metal pipe to be tested, a specific phase difference of an undamaged metal pipe is detected by the third receiving coil to compare it with the reference phase difference of the reference metal pipe having the same thickness to obtain a correction factor which corresponds to the material of the metal pipe, after which the metal pipe is tested. A phase change of the magnetic field detected by the first and second receiving coils is corrected by the correction factor to be converted into the reference phase difference of the reference metal pipe and the thickness of the metal pipe is obtained from the relationship between the reference phase difference and the thickness of the reference metal pipe. Accordingly, the existence of a flaw and the depth of the flaw may be accurately detected in accordance with the difference of materials of the metal pipe.

The above and other related objects and features of the present invention will be apparent from a reading of the following description of the disclosure found in the accompanying drawings and the novelty thereof pointed out in the appended claims.

DETAILED DESCRIPTION OF PREFERRED EMBODIMENT

A preferred embodiment of a flaw sensor for metal pipes of the present invention will be explained below with reference to the drawings.

Figure 1:
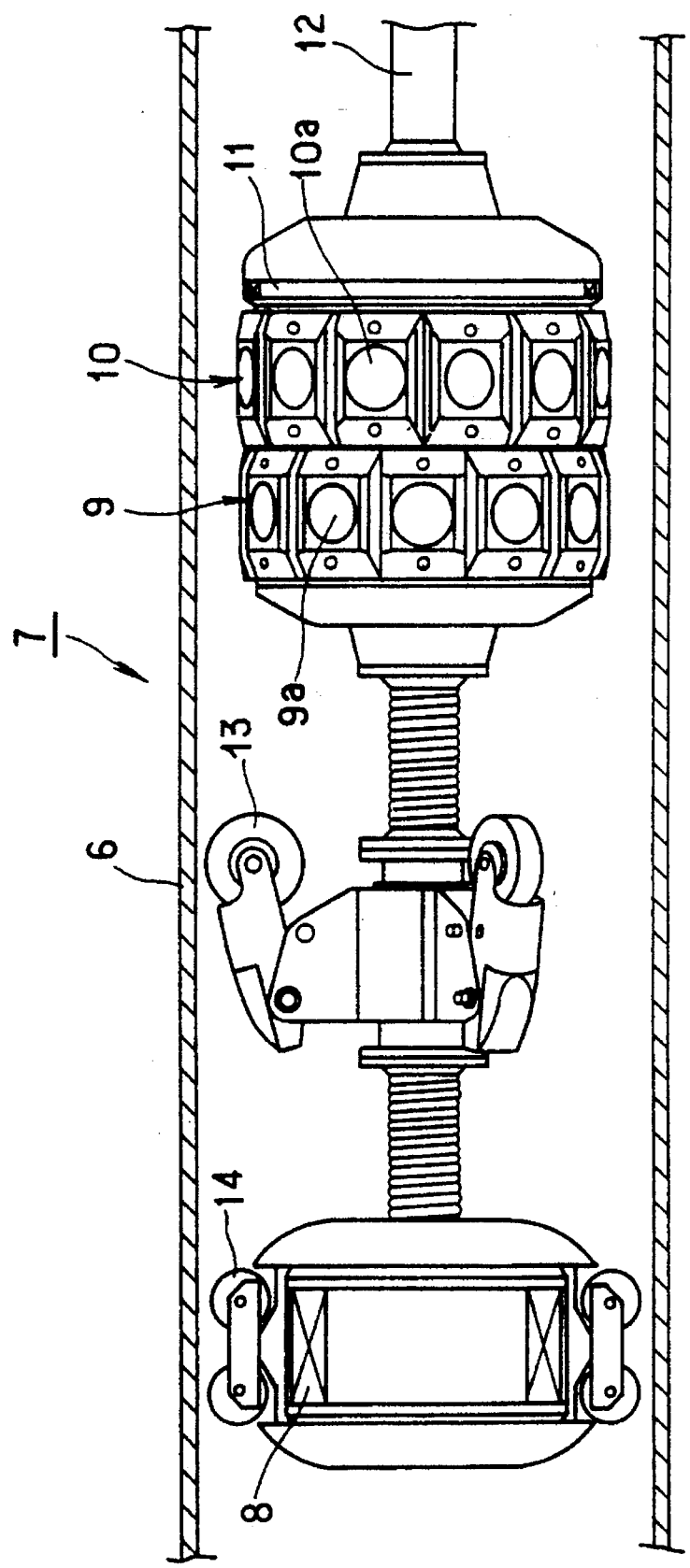
FIG. 1 is a side view illustrating one embodiment of a flaw sensor for metal pipes of the present invention.

As shown in FIG. 1, a remote field eddy current sensor 7 which is a flaw sensor for metal pipes and which is inserted into a metal pipe 6 to test interior and exterior walls thereof is equipped with an exciting coil 8 having an axis coaxial to an axis of the metal pipe 6, a first receiving coil group 9 spaced apart from the exciting coil 8 by a predetermined distance which is about twice the diameter of the pipe, a second receiving coil group 10 disposed behind the first receiving coil group 9 in the vicinity thereof and a third receiving coil 11 disposed behind the second receiving coil group 10. The remote field eddy current sensor 7 is attached to a signal transmission cable 12 to transmit/receive signals to/from equipment (FIG. 4) outside the metal pipe. The remote field eddy current sensor 7 is also provided with driving wheels 13 pressed against the interior wall of the metal pipe 6 by springs or the like and controlled by a driving unit (not shown) outside the pipe in, for example, three directions along the inner circumference of the pipe to allow the sensor 7 to run within the metal pipe while supporting it and controlling and monitoring the directions and rotations of the driving wheels 13.

The exciting coil 8 of the remote field eddy current sensor 7 is held within the metal pipe 6 by driving wheels 14. An exciting signal normally having a relatively low frequency from several tens of hertz to several hundreds of hertz is applied to the exciting coil 8 via the signal transmission cable 12 with a desired exciting voltage, e.g. a voltage from several volts to several tens of volts. Then, a magnetic field caused by a remote field eddy current is generated from the exciting coil 8 to which the exciting signal has been applied. While a part of the generated magnetic field propagates within the pipeline and rapidly attenuates, the other part thereof passes through the thickness of the metal pipe and gradually attenuates. It propagates in parallel with the axis of the pipe at a sound part of the metal pipe where there is no flaw.

Figure 2:
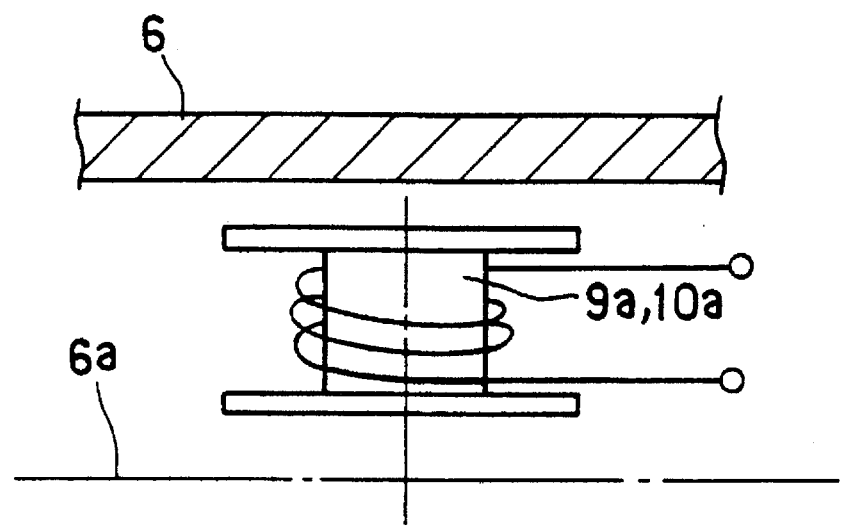
FIG. 2 is a schematic drawing illustrating a main part of the embodiment shown in FIG. 1.

The first receiving coil group 9 is equipped with twelve first receiving coils 9a at predetermined intervals, e.g. every 30°, along the inner circumference of the pipe distant from the exciting coil 8 by a predetermined distance. The first receiving coils 9a have their axes at right angles to the axis 6a of the metal pipe 6 as shown in FIG. 2.

When AC power is supplied to the exciting coil 8, a magnetic field is generated around the exciting coil 8. It propagates within the thickness of the metal pipe 6 and transmits as a reception signals. When no flaw exists in the metal pipe 6, the reception signal propagating within the thickness of the pipe runs in parallel with the axis of the pipe and almost no component exists in the direction of pipe diameter which crosses the axis of pipe at right angles. When there is a flaw on the metal pipe 6 on the other hand, the flow of the magnetic flow is disturbed by the flaw and the component in the direction of pipe diameter appears.

Due to this, when there is no flaw in the metal pipe 6, the first receiving coil 9a receives almost no reception signal because the axis of the first receiving coil 9a is at right angles to the magnetic field which propagates passing through the thickness of the metal pipe. Conversely, when there is a flaw in the metal pipe 6, the first receiving coils 9a can receive the reception signal generated at the defective portion and reliably detect even a very weak magnetic field generated at a very small defective portion because its axis runs parallel with the magnetic field generated at the defective portion. Thereby, the damaged portion generated in the metal pipe may be detected effectively.

Figure 3:
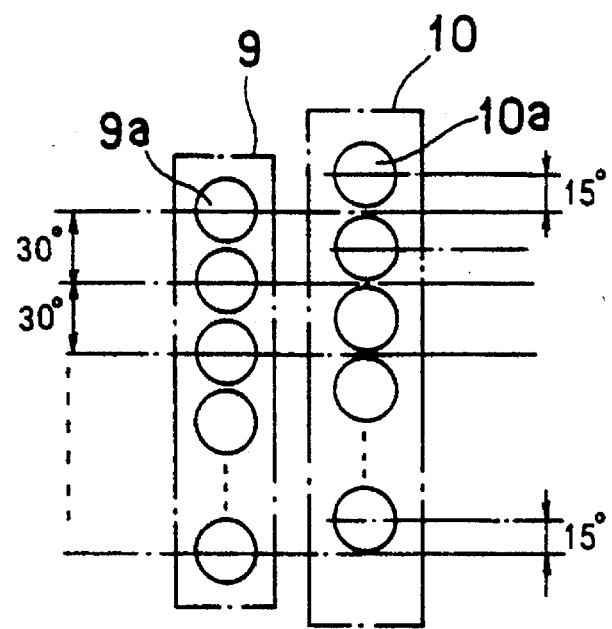
FIG. 3 is a schematic diagram illustrating a main part of the embodiment shown in FIG. 1.

The second receiving coil group 10 comprises a plurality of second receiving coils 10a (see FIG. 2) whose axes are at right angles to the axis 6a of the metal pipe 6 similarly to the first receiving coils 9a and which reliably receive a magnetic field generated at a defective portion. The second receiving coil group 10 is disposed at a predetermined distance from the first receiving coil group 9 and is equipped with twelve receiving coils 10a at predetermined intervals, e.g. every 30°, along the inner circumference of the pipe. As shown in FIG. 3, the second receiving coils 10a are disposed at positions staggered from the first receiving coils 9a in the circumferential direction of the pipe by a predetermined angle (15° in this case), i.e. at so-called staggered positions. Due thereto, the first receiving coils 9a and the second receiving coils 10a are disposed along the entire circumference of the pipe every 15° in the circumferential direction of the pipe. Therefore, even when a flaw in the wall of the metal pipe passes between the first receiving coils 9a of the first receiving coil group 9 and is therefore not detected by the first receiving coil group 9, a second receiving coil 10a of the second receiving coil group 10 will pass right above the flaw. That is, a flaw on undetected zones of the first receiving coil group 9 may be detected by the second receiving coil group 10, allowing testing of the entire circumference of the wall of the metal pipe by a single scan.

The single third receiving coil 11 is disposed coaxially with the axis of the pipe at a predetermined distance from the exciting coil 8. It fully receives the reception signal of the magnetic field in the direction parallel to the axis of the pipe which propagates through the sound portion thereof. However, the third receiving coil 11 hardly receives the magnetic field perpendicular to the axis of pipe generated when there is a flaw in the metal pipe because its axis is not parallel to the magnetic field and it is composed of one coil. Therefore, the third receiving coil 11 is not substantially affected by the existence of the defective portion on the metal pipe and receives a constant reception signal of the magnetic field generated from the exciting coil 8 and propagating through the thickness of the metal pipe 6 regardless of the existence of a defective portion.

Figure 4:
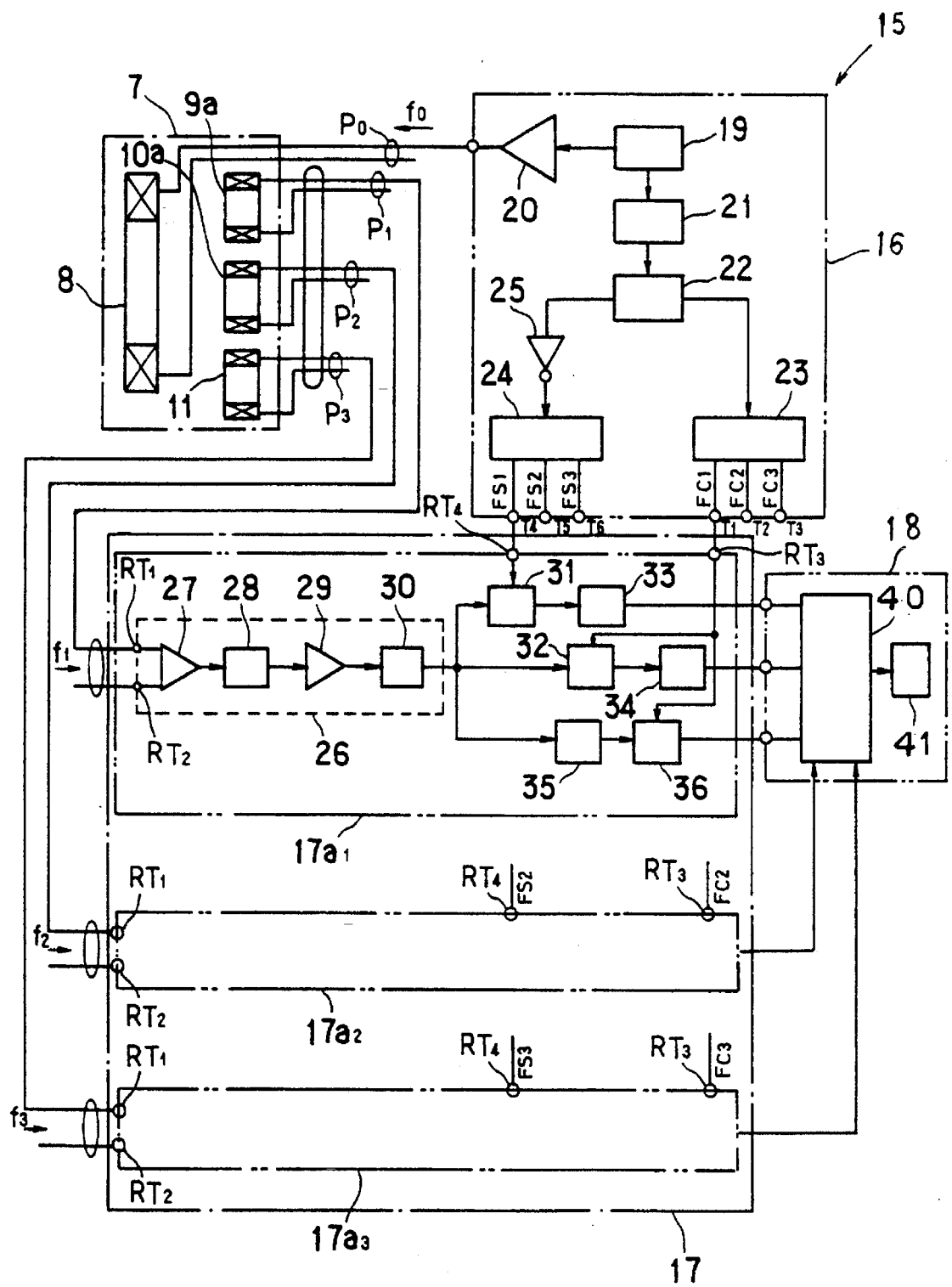
FIG. 4 is a block diagram illustrating a flaw detector or discriminator for metal pipes to which the embodiment shown in FIG. 1 is applied.

The remote field eddy current sensor 7 described above is applied to the flaw detector for metal pipes to detect a flaw the metal pipe. As shown in FIG. 4, a flaw detector for metal pipes 15 comprises an exciting signal transmitting circuit 16 for applying the exciting signal to the exciting coil 8 of the remote field eddy current sensor 7, a measured signal processing circuit 17 for receiving measured signals from each of the first receiving coils 9a, the second receiving coils 10a and the third receiving coil 11 of the remote field eddy current sensor 7 and a flaw data producing circuit 18 for creating detected flaw data from an output of the measured signal processing circuit 17. The flaw detector 15 is also equipped with a monitoring mechanism (not shown) for monitoring the remote field eddy current sensor 7 and a driving unit (not shown) for allowing the remote field eddy current sensor 7 to travel within the pipe while monitoring the remote field eddy current sensor 7.

Note that although only one of each of the first receiving coils 9a and the second receiving coils 10a are shown in the figure, actually there are twelve coils each and although measurement modules 17a, and 17a₂ in the measured signal processing circuit 17 for processing the measured signals from the first receiving coils 9a and the second receiving coils 10a are provided in correspondence with each receiving coil, only one of each of them is shown in the figure and the others are omitted here in order simplify explanation.

The exciting signal transmitting circuit 16 comprises a reference transmitter 19 for transmitting an exciting signal $f_o$ and an exciting signal power amplifier 20 for amplifying and sending the exciting signal $f_o$ transmitted from the reference transmitter 19. The exciting signal power amplifier 20 is connected to the exciting coil 8 via an exciting side terminal $T_o$ by a paired cable $P_o$. The exciting signal transmitting circuit 16 is also equipped with a wave-shaping circuit 21 for converting the wave of the exciting signal $f_o$ transmitted from the reference transmitter 19 into a rectangular wave and a frequency multiplier 22 for converting the rectangular wave from the wave-shaping circuit 21 into a wave having a double frequency. It is also equipped with flip-flops 23 and 24 to which outputs from the frequency multiplier 22 are input, respectively. The signal input to the flip-flop 24 is input via an inverter 25 which inverts it. Reference signals $FC_1$, $FC_2$ and $FC_3$ and reference signals $FS_1$, $FS_2$ and $FS_3$ which are returned to their respective original frequencies by the flip-flops 23 and 24 have phases which are shifted by 90° from each other and are sent to the measured signal processing circuit 17 via the exciting side terminals $T_1$, $T_2$, $T_3$, $T_4$, $T_5$ and $T_6$ respectively. The reference signals $FC_1$, $FC_2$, $FC_3$, $FS_1$, $FS_2$ and $FS_3$ are signals in which each phase lag from the exciting signal $f_0$ of the measured signals $f_1$, $f_2$ and $f_3$, which are transmitted respectively from the first receiving coils 9a, the second receiving coils 10a and the third receiving coil 11 of the remote field eddy current sensor 7 to the measured signal processing circuit 17, is corrected. Note that the reference signal $F_1$ may have the same phase as that of the exciting signal $f_0$ when a special cable is used for the pair core wires $P_0$, $P_1$, $P_2$ and $P_3$ for transmitting the exciting signal $f_0$ and the measured signals $f_1$, $f_2$ and $f_3$.

The measured signal processing circuit 17 has the measured signal processing module $17a_1$ connected to the first receiving coils 9a via measurement side terminals $RT_1$ and $RT_2$ by the paired cable $P_1$, the measured signal processing module $17a_2$ connected to the second receiving coils 10a via measurement side terminals $RT_1$ and $RT_2$ by the paired cable $P_2$ and the measured signal processing module $17a_3$ connected to the third receiving coil 11 via: measurement side terminals $RT_1$ and $RT_2$ by the paired cable $P_3$. Each of the measured signal processing modules $17a_1$, $17a_2$ and $17a_3$ is equipped with a measured signal interface 26 for inputting the measured signals transmitted from the respective receiving coils via the measurement side terminals $RT_1$ and $RT_2$. The measured signal interface 26 comprises, sequentially, a differential amplifier 27 for removing homopolar noises generated in the paired cable $P_1$ or the like, a low-pass filter for removing a high frequency component, a receiving amplifier 29 for amplifying the signal from the low-pass filter 28 and a band-pass filter 30 for removing frequency components out of a certain area to limit the input measured signal to a signal having a frequency within a predetermined range. Provided also on the output end of the measured signal interface 26 are two synchronous detectors or discriminators 31 and 32.

The synchronous detector 31 is arranged so that another input thereof is connected with a measurement side terminal $RT_4$ which is connected with the exciting side terminal $T_4$ of the exciting signal transmitting circuit 16 to input the reference signal $FS_1$. Similarly, another input of the synchronous detector 32 is connected with a measurement side terminal $RT_3$ which is connected with the exciting side terminal $T_1$ of the exciting signal transmitting circuit 16 to input the reference signal $FC_1$. Wave-shaping circuits 33 and 34 are respectively connected to the output ends of the synchronous detectors 31 and 32 to full-wave rectify to direct current and to Send to the flaw data producing circuit 18. On the other hand, a wave-shaping circuit 35 for shaping the input signal into a certain waveform is provided on the output end of the measured signal interface 26 and the measured signal from the receiving coil is converted into a constant waveform having predetermined frequency and amplitude. Provided on the output end of the wave-shaping circuit 35 is a phase detecting circuit 36 whose another input end is connected to the exciting side terminal $T_1$ via the measurement side terminal $RT_3$ to input the reference signal $FC_1$ to compare with the phase of the measured signal $f1$ to detect the phase differences of the measured signal $f_1$ and the exciting signal $f_o$. An output end of the phase detecting circuit 36 is connected to the flaw data producing circuit 18 to send the detected phase differences to the flaw data producing circuit 18 together with the signals from the wave-shaping circuits 33 and 34.

The measured signal processing nodules $17a_2$ and $17a_3$ each have the same structure as that of the measured signal $17a_1$, input the measured signals $f_2$ and $f_3$ from the second receiving coils 10a and the third receiving coil 11 and process them in the same manner and send them to the flaw data producing circuit 18.

The flaw data producing circuit 18 comprises a computing element 40 for computing the thickness of the metal pipe from the input phase difference to detect the existence of defective portions and the depths of flaws, and a display section 41 for displaying a rate of decrement of the thickness computed by the computing element 40.

The phase difference between the exciting signal applied to the exciting coil and the measured signal obtained from the receiving coil may be expressed as follows.

$$\theta = k\sqrt{\pi f \mu \sigma} \tag{1}$$

Here, θ represent the phase difference, k a proportional constant, π the ratio of the circumference of a circle to its diameter, f the frequency of the exciting signal, μ the permeability of the metal pipe and σ the conductivity of the metal pipe.

Figure 5:
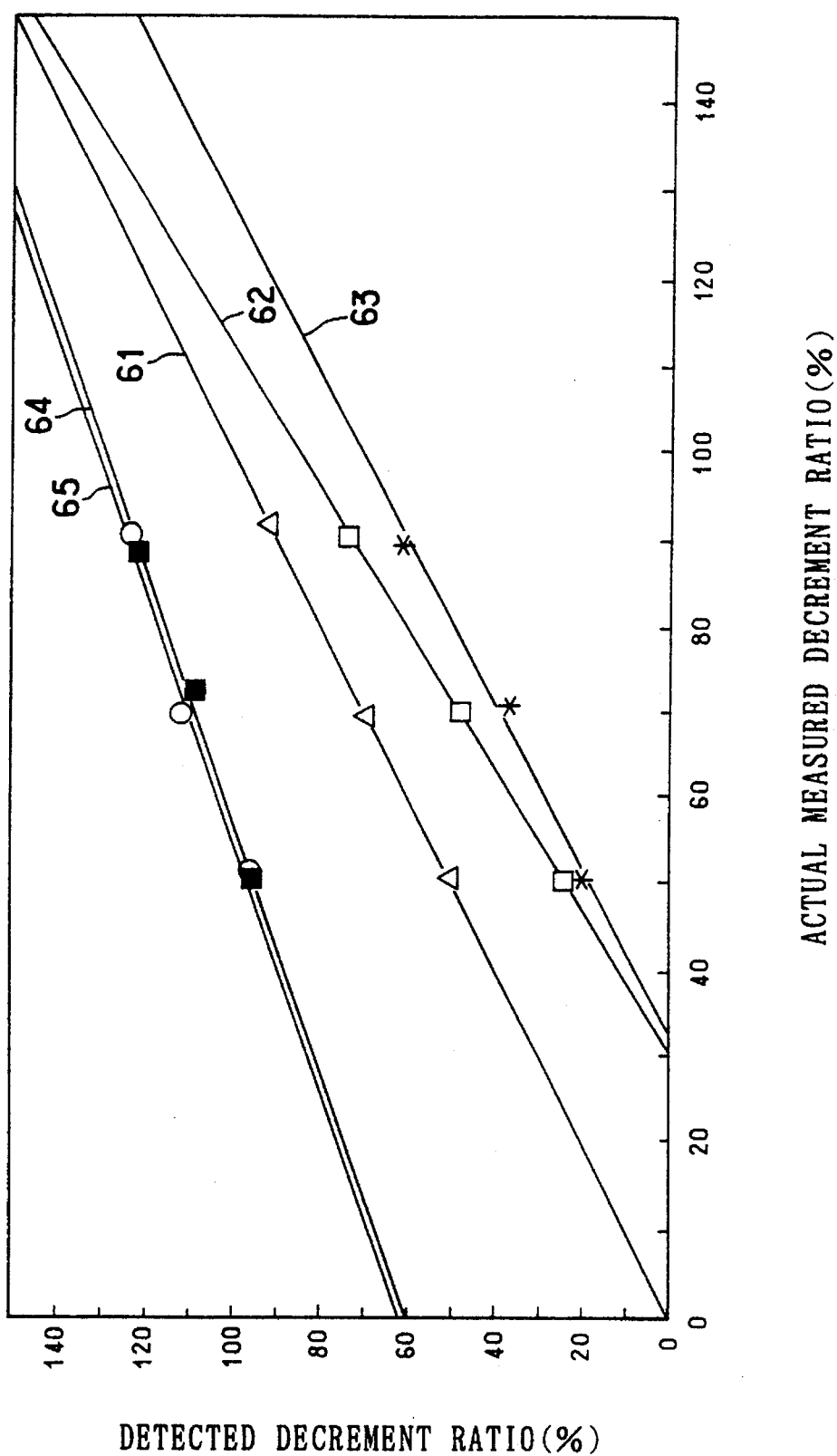
FIG. 5 is a graph showing errors of detected thicknesses caused by the difference of magnetic characteristics of metal pipes.

As it is apparent from Equation (1), the phase difference of the measured signal changes depending on the permeability μ times the conductivity σ of the metal pipe and the frequency of the exiting signal applied to the exciting coil. Among them, permeability μ times conductivity σ is intrinsic to the material of the pipe. Due thereto, however the phase difference of the measured signal of the receiving coil is proportional to the thickness of the pipe, an erroneous result is brought about if the thickness is derived based uniformly on the obtained phase difference. FIG. 5 shows a relationship between a thickness (decrement ratio) of a defective portion detected based on the phase difference of the measured signal and an actual thickness (decrement ratio) of several kinds of metal pipes 61, 62, 63, 64 and 65 having the same shape and thickness and different products of permeability μ times conductivity σ. As is apparent from the figure, the detected thicknesses differ from the actual thicknesses even though metal pipes having the same shape and thickness have been used.

The phase difference of the measured signal caused by the difference of materials even though metal pipes having the same thickness are used may be offset and thickness derived uniformly from the detected phase difference by the following method. That is, flaw detection is carried out by changing the frequency of an exciting signal applied to the exciting coil depending on the material of the metal pipe so that a phase difference detected from the metal pipe to be detected becomes the same as that of the measured signal detected from a reference metal pipe having the same thickness, i.e. the phase difference θ in Equation 1 becomes a value of the phase difference of the reference metal pipe. A magnetic field is generated in a sample metal pipe of the same material as the metal pipe to be detected and having the same thickness as that of the reference metal pipe by applying an exciting signal by changing its frequency to change the phase difference thereof and to detect in advance a specific frequency when a phase difference which is equal to the phase difference of the measured signal of the reference metal pipe is obtained. Then the metal pipe is scanned by the exciting signal having the specific frequency. The phase difference θ of the signal to be measured becomes a phase difference θ which corresponds to the thickness of the reference metal pipe. Accordingly, accurate flaw data may be obtained for the metal pipe, even if permeability μ times conductivity σ differs, by finding the thickness from the relationship between the phase difference and the thickness of the reference metal pipe measured in advance.

Figure 6:
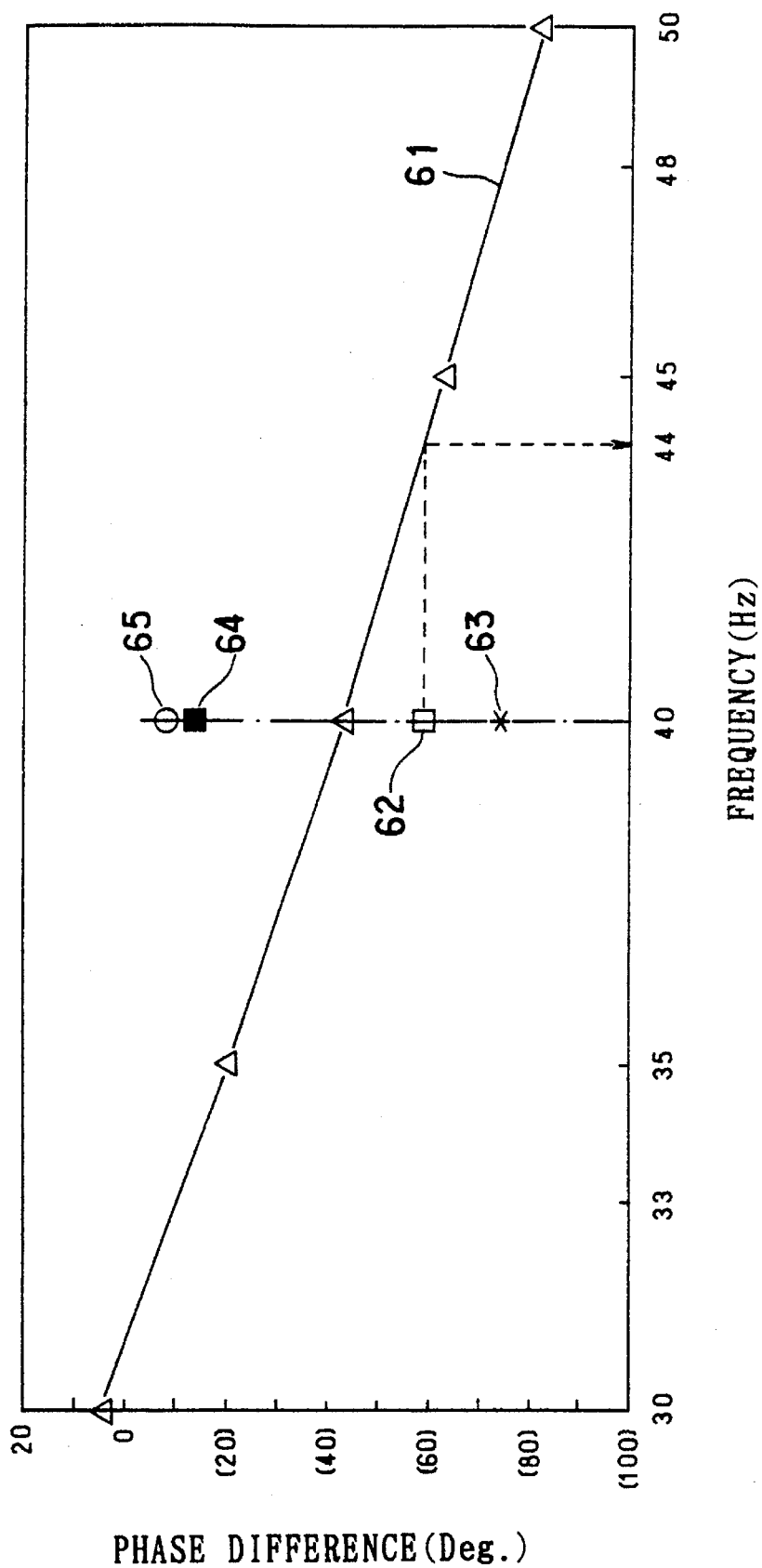
FIG. 6 is an explanatory chart for practicing the metal pipe flaw detection method of the present invention.
Figure 7:
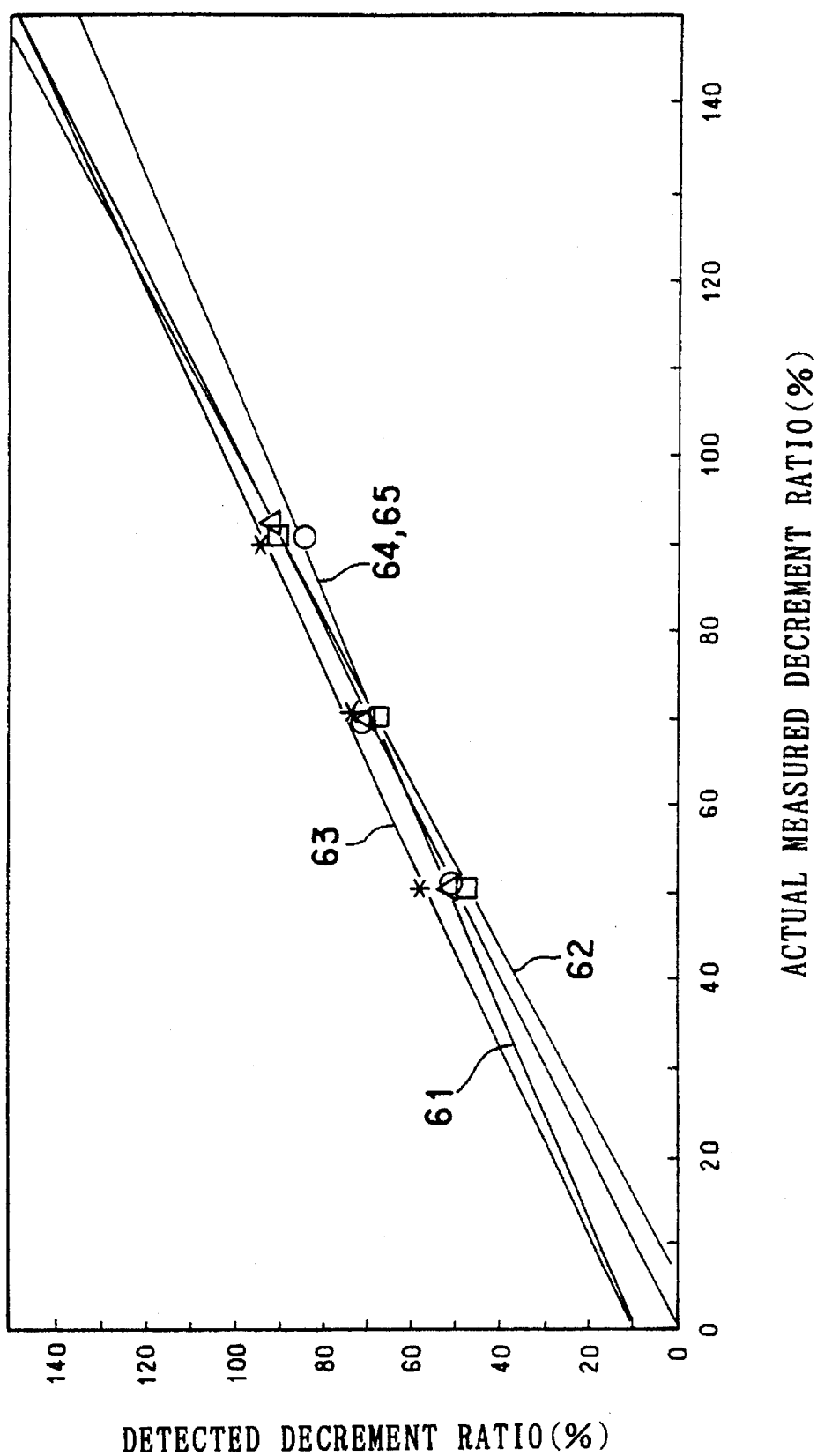
FIG. 7 is a graph showing errors of detected values of the metal pipe flaw detection method of the present invention.
Figure 8:
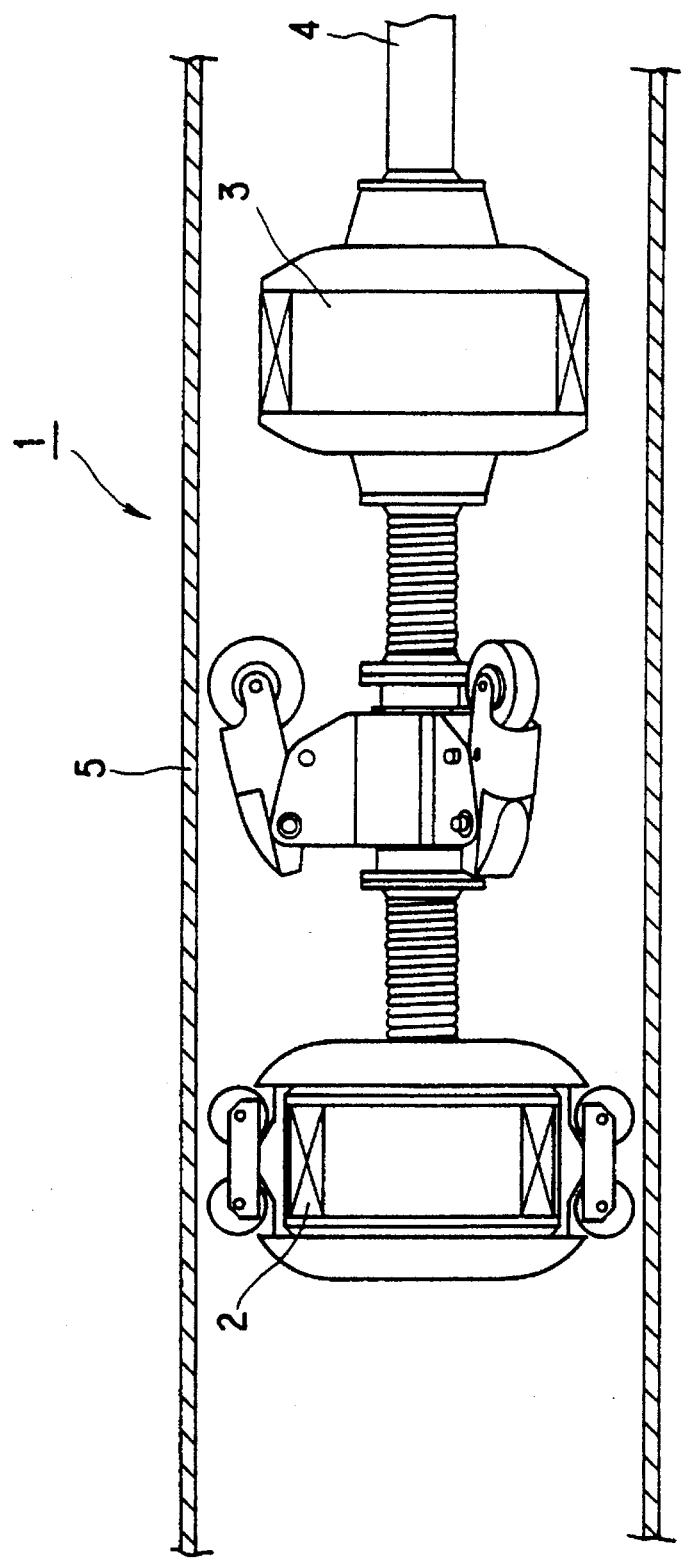
FIG. 8 is a side view illustrating a prior art remote field eddy current sensor.

As another method, flaw detection may be carried out assuming that the frequency of the exciting signal applied to the exciting coil is a constant frequency H and by making the following correction. As shown in FIG. 6, a relationship between the frequency of the exciting signal applied to the exciting coil and the phase difference of the measured signal (reference phase difference) of a reference metal pipe 61 having a constant thickness is detected in advance. Then, for the metal pipe 62 which is to be detected, an exciting signal having a constant frequency Hz (40 Hz in the drawing) is applied to an undamaged sample metal pipe having no defective portions (thickness (d)) in advance to detect the phase difference of the measured signal of the receiving coil obtained at that time as a specific phase difference (about −60° C.). A frequency Ha (about 44 Hz) which is applied to the reference metal pipe when the reference phase difference similar to the specific phase difference is obtained from the relationship between the frequency of the exciting signal and the reference phase difference Of the reference metal pipe to be referred to is obtained to Calculate a correction factor H/Ha as a ratio between the frequency Ha and the constant frequency H. The phase difference of the measured signal obtained when the metal pipe is detected is corrected by this correction factor, i.e. the measured phase difference is multiplied by the correction factor H/Ha to derive a phase difference which corresponds to the thickness of the reference metal pipe, and the thickness of the metal pipe being scanned is found from the relationship between the reference phase difference and the thickness of the reference metal pipe. Such correction allows correction even when a metal pipe having a different permeability μ times conductivity σ to the relationship which corresponds to the reference phase difference and the thickness of the reference metal pipe, and can consistently obtain accurate flaw data. When the correction factor is detected and the thickness detected from the phase difference corrected by the correction factor in the same manner as for the other metal pipes 63, 64 and 65, the relationship between the detected thickness and the actual thickness resulting therefrom is as shown in FIG. 7. It is apparent also from the figure that thicknesses which substantially coincide with the actual thicknesses are detected.

An operation of the flaw detector for metal pipes 15 for executing the method of offsetting the phase difference of the measured signal caused by the difference of materials and of deriving the thickness uniformly based on the detected phase difference described above will be explained.

First, a frequency of an exciting signal applied to the exciting coil, a phase difference of a measured signal and a relationship between the phase difference and a thickness of a reference metal pipe are input to the flaw data producing circuit 18 in advance. Then, the remote field eddy current sensor 7 is inserted into the metal pipe 6 to be detected by the driving unit. Next, an exciting signal $f_o$ having a frequency H is generated from the reference transmitter 19 to be applied to the exciting coil 8 via the exciting side terminal $T_o$ and sent to the frequency multiplier 22 via the wave-shaping circuit 21. After being converted to a double frequency, the signal is converted to the original frequency again by the flip-flops 23 and 24 and sent to the measured signal processing modules $17a_1$, $17a_2$ and $17a_3$ via the exciting side terminals $T_1$ to $T_6$. Because the signal input to the flip-flop 24 is inverted by the inverter 25 at this time, the reference signals $FS_1$, $FS_2$ and $FS_3$ have phases which are shifted by 90 from that of the reference signals $FC_1$, $FC_2$ and $FC_3$ output from the flip-flop 23.

The measured signals $f_1$, $f_2$ and $f_3$ transmitted respectively from the first receiving coils $9a$, the second receiving coils $10a$ and the third receiving coil 11, to which the magnetic field caused by the remote field eddy current generated in the metal pipe by the exciting signal $f_0$ applied to the exciting coil 8 is input, are output. When the measured signals are input to the measured signal processing modules $17a_1$, $17a_2$ and $17a_3$, are shaped into signals having a predetermined range of frequency by the measured signal interface 26, input to two synchronous detectors 31 and 32, and detected by the reference signals $FC_1$, $FC_2$ and $FC_3$ having different phases. Even when the magnetic field received by the first receiving coils $9a$ and the second receiving coils $10a$ at the sound part of the metal pipe becomes almost zero, output thereof is stabilized by synchronous detection by the reference signals $FC_1$ and $FC_2$ and the reference signals $FS_1$ and $FS_2$ whose phases differ by 90°. That is, when the measured signal is zero, the output becomes zero and when a certain level of measured signal exists, a corresponding output may be obtained. Similarly, even when the magnetic field received by the third receiving coil 11 at the defective portion of the metal pipe becomes almost zero, the output is stabilized by synchronous detection by the reference signals $FC_3$ and $FS_3$. That is, when the measured signal is zero, the output becomes zero and when a certain level of measured signal exists, a corresponding output may be obtained. The outputs from the synchronous detectors 31 and 32 are full-wave rectified by the wave-shaping circuits 33 and 34, respectively, and are then sent to the flaw data producing circuit 18.

On the other hand, the measured signals from the first, second and third receiving coils are wave-shaped by the wave-shaping circuit 35 into a certain waveform having a predetermined frequency and amplitude. Then, their phases are compared with the reference signal FC, by the phase detecting circuit 36. The phase difference between the measured signal $f_1$ and the exciting signal $f_0$ is detected and output to the flaw data producing circuit 18 to be processed together with the full-wave rectified signals from the wave-shaping circuits 33 and 34.

In the flaw data producing circuit 18, the input signal from the measured signal processing module $17a_3$ is processed by the computing element 40 to detect a specific phase difference of the metal pipe. Then, a correction factor is computed from the specific phase difference by comparing it with the reference phase difference input in advance.

When there is no flaw in the wall of the metal pipe 6, the outputs from the measured signal processing modules $17a_1$ and $17a_2$ become zero and nothing is displayed on the display section 31 of the flaw data producing circuit 18. When there is a flaw in the wall of the metal pipe 6, a phase difference from the measured signal processing modules $17a_1$ and $17a_2$ is detected. The phase difference is input to the computing element 40 of the flaw data producing circuit 18 and is multiplied by the correction factor to be corrected to the reference phase difference. The thickness at that time is detected from the relationship between the reference phase difference and the thickness input in advance and is displayed on the display section 41. Therefore, an accurate thickness may be detected no matter what kind of material is used for the metal pipe.

It should be noted that the above description has been given to explain one preferred embodiment of the present invention and that the present invention is not confined thereto. That is, although the first receiving coil, second receiving coil and third receiving coil have been represented as an absolute value system, they may be a differential system comprising two pairs in front and rear.

As it is apparent from the above description, the flaw sensor for metal pipes of the present invention comprises first and second receiving coils whose axes are at right angles to an axis of a metal pipe and a third receiving coil whose axis is parallel to the axis of the metal pipe, so that a magnetic field generated in a sound part of the metal pipe may be received by the third receiving coil and a disturbance of the magnetic field generated by a defective portion may be received effectively by the first and second receiving coil groups. Further, because the second receiving coils are staggered from the first receiving coils, i.e. the receiving coils are disposed around the entire inner circumference of the pipe, it becomes possible to detect whether a flaw exists by a single scan.

Further, the flaw detection method for metal pipes of the present invention allows elimination of a detection error which may be caused by a phase difference which changes due to a difference in the material of the metal pipe due to magnetic characteristics and to evaluate the existence of corrosion generated in the metal pipe and the depth of a flaw accurately corresponding to the material of the metal pipe by correcting the phase difference of the measured signals obtained for the metal pipe so as to correspond to the phase difference of measured signals obtained for the reference metal pipe and by detecting the thickness of the metal pipe from the relationship between the phase difference of the measured signals and the thickness of the reference metal pipe.

While one preferred embodiment has been described, variations thereto will occur to those skilled in the art within the scope of the present inventive concepts which are delineated by the following claims.

What is claimed is:

1. A flaw sensor for metal pipes, comprising:

an exciting coil for generating a remote field eddy current in a metal pipe when an exciting signal is applied thereto;

a first receiving coil group comprising a plurality of first receiving coils which are separated from said exciting coil by a predetermined distance in the longitudinal direction of said metal pipe, whose axes are perpendicular to the longitudinal direction of said metal pipe and which are disposed at predetermined intervals in the circumferential direction of said metal pipe to receive reception signals caused by said remote field eddy current in a defective portion of said metal pipe;

a second receiving coil group comprising a plurality of second receiving coils which are separated from said exciting coil and said first receiving coil group by predetermined distances, whose axes are perpendicular to the longitudinal direction of said metal pipe and which are disposed at predetermined intervals in the circumferential direction of said pipe in positions staggered from said first receiving coils to receive reception signals caused by said remote field eddy current in a defective portion of said metal pipe; and a third receiving coil disposed coaxially with said metal pipe, said third receiving coil being not substantially affected by the existence of a defective portion of the pipe and receiving a constant reception signal of the magnetic field generated from the exciting coil and propagating through the thickness of the pipe regardless of the existence of a defective portion of the pipe.

2. A flaw detecting method for metal pipes, comprising the steps of:

generating a remote field eddy current in a metal pipe having a defective portion and a non-defective portion by applying an exciting signal to an exciting coil which is coaxial with the metal pipe;

generating first reception signals from a magnetic field generated at said remote field eddy current perpendicular to the longitudinal direction of said metal pipe at the defective pipe portion by a first receiving coil having a axis perpendicular to the longitudinal direction of said damaged metal pipe to detect the defective portion of said metal pipe;

detecting a first phase difference between the first reception signals and said exciting signal;

generating second reception signals from a magnetic field generated at said remote field eddy current at both the defective portion and the non-defective portion by a third receiving coil having an axis coaxial to the longitudinal direction of said metal pipe;

detecting a second phase difference between the second reception signals and said exciting signal; and determining a thickness of the defective portion of said metal pipe from said first phase difference and said second phase difference.

3. The flaw detecting method for metal pipes according to claim 2 wherein the first reception signals are generated by one or more coils in first and second groups of coils which are separated from the exciting coil by predetermined distances in the longitudinal direction of the metal pipe so as to be disposed at the remote field eddy current, said first and second groups of coils having axes perpendicular to the longitudinal direction of said metal pipe and being disposed at predetermined intervals in the circumferential direction of said metal pipe with the coils of the second group being staggered relative to the coils of the first group.

4. A flaw detecting method for metal pipes comprising the steps of:

generating remote field eddy currents in metal pipes by applying an exciting signal to a exciting coil;

generating first reception signals caused by said remote field eddy currents by a first receiving coil coaxial with the metal pipes;

producing a reference phase difference and a pipe wall thickness relationship from a phase difference of the first reception signals from the exciting signal in a reference metal pipe;

producing a specific phase difference from a difference of the first reception signals from the exciting signal in a subject pipe having a standard wall thickness;

determining a correction factor from the reference phase difference and the specific phase difference;

generating second reception signals from a magnetic field generated at the remote field eddy currents perpendicular to the longitudinal direction in the second subject pipe at the defective pipe portion by a first receiving coil having a axis perpendicular to the longitudinal direction of said second subject pipe to detect the defective portion of said second subject pipe;

detecting a subject phase difference between said exciting signal and one of the first and second reception signals;

correcting the subject phase difference by said correcting factor to produce a corrected phase difference; and detecting a thickness of the defective portion of said metal pipe from the corrected phase difference and the relationship of the thickness of said reference metal pipe.

* * * * *